United States Patent [19]

Lim

[11] Patent Number: 5,769,671
[45] Date of Patent: Jun. 23, 1998

[54] CONNECTOR SPRING

[75] Inventor: Wisit Lim, Palmdale, Calif.

[73] Assignee: Pacesetter, Inc.

[21] Appl. No.: 795,920

[22] Filed: Feb. 5, 1997

[51] Int. Cl.$^6$ .................................................. H01R 13/53
[52] U.S. Cl. .......................................... 439/843; 439/851
[58] Field of Search .................................... 439/843, 846,
439/851, 909, 346, 350, 675; 607/37, 116,
119

[56] References Cited

U.S. PATENT DOCUMENTS

| 2,317,023 | 4/1943 | Bird | 173/363 |
|---|---|---|---|
| 2,659,876 | 11/1953 | Dupre et al. | 439/846 |
| 2,750,543 | 6/1956 | Wadsworth | 317/236 |
| 4,120,557 | 10/1978 | Horrocks | 439/843 |
| 4,550,972 | 11/1985 | Romak | 339/256 R |
| 4,687,278 | 8/1987 | Grabbe et al. | 439/842 |
| 4,767,360 | 8/1988 | Bonhomme | 439/593 |
| 4,874,338 | 10/1989 | Bakermans | 439/851 |
| 5,221,220 | 6/1993 | Roscizewski | 439/843 |
| 5,409,388 | 4/1995 | Phillips, Jr. et al. | 439/125 |

FOREIGN PATENT DOCUMENTS

| 1473224 | 2/1967 | France . | |
| 326887 | 10/1920 | Germany | 439/851 |

Primary Examiner—Neil Abrams
Assistant Examiner—Tho D. Ta

[57] ABSTRACT

A contact spring is provided within a connector for use in a pacemaker having a radially deflectable projections enhancing contact with an inserted lead and is square shaped so as to fit within an annular extending gap in the housing so that the corners of the square shape of the spring are captured within the annular gap and prevents pull out of the spring when an electrical lead is inserted or removed.

12 Claims, 3 Drawing Sheets

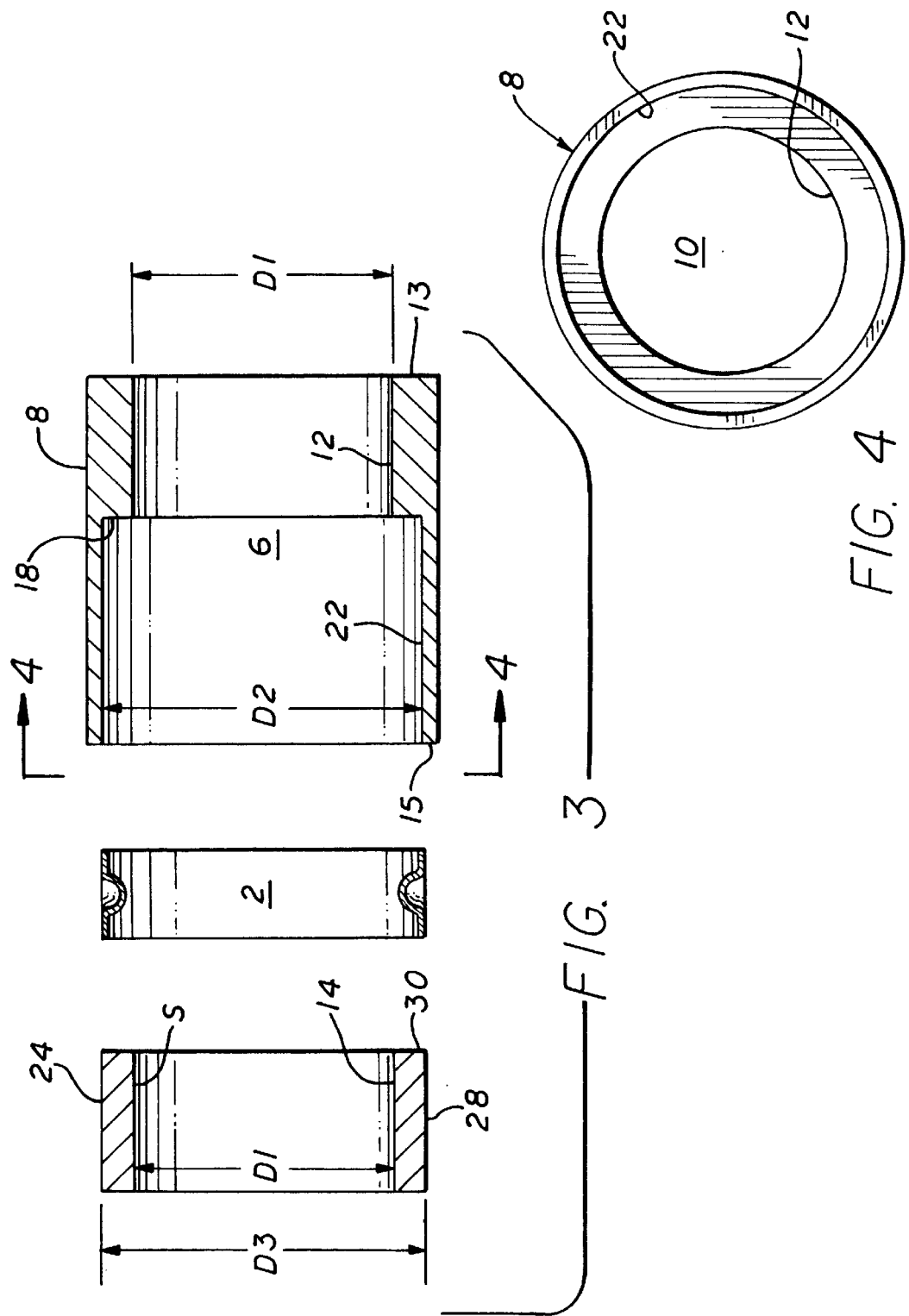

CONNECTOR SPRING

FIELD OF THE INVENTION

This invention relates generally to a connector for connecting two axially oriented electrical conductors to one another, and deals more particularly with an improvement in such connectors whereby a contact spring is provided as part of the connector to engage and compress around the axially inserted member received within the connecter to provide among other things, enhanced electrical contact between the two connected parts.

BACKGROUND OF THE INVENTION

A pacing system is comprised of essentially three elements, namely, a pulse generator, a lead system, and an electrical interface. The pulse generator is an implantable device that contains a battery, circuit, and other components which provide the output stimuli. The lead system, which is comprised of insulated wires, is used to connect the pulse generator to the cardiac tissue. The lead carries the output stimulus from the pulse generator to the heart and in demand modes, relays native or intrinsic cardiac signals back to the sense amplifier of the pulse generator. The type of pulse generator may require one or two chambers, and hence an equal number of leads connecting to the pulse generator depending on whether the atrium or ventricles are being stimulated separately or together. Finally, the pacing system includes an electrode interface which includes a lead which connects to the cardiac tissue.

Electrical connections, particular those used in the connection between a pacemaker implant and a lead, must provide an electrical connection to insure a constantly available stimulus to the cardiac tissue. In addition to this most basic requirement, such connectors must be adapted for use and operation in the human body. Such connectors must also be compact in size because the environment in which the connector is used is very tight. In addition, the mechanical connection between the connected part must be such that repeated connect and disconnect operations between the connected parts does not cause the connecting spring of the connector to become dislodged with the extraction of the lead.

Also, in the past, the connection between the pacemaker and one or more leads which connect to it, has involved using a leaf spring to provide a positive contacting force between the lead and the pacemaker to insure that electrical contact is always maintained therebetween. The use of such leaf springs or bal-seal springs in connectors of this type is however problematic for two reasons. First, as discussed previously, space limitation is an important concern. In using a leaf spring in a connector, the connector top assembly must be dimensioned length and widthwise so as to be sufficiently sized to allow the leaf spring to deflect to thus effect the desired connection. Second, use of such bal-seal springs has been problematic in that such springs have been prone to pull-out with the extraction of a lead from the connector.

Accordingly, it is an object of the present invention to provide a contact spring within an electrical connector which is capable of making reliable electrical connections in the limited space of a pacer implant.

It is still a further object of the invention to provide a connector of the aforementioned type wherein the contact spring is radially deflectable with the insertion of an electrical lead and does not pull out from the connector housing upon the extraction of the lead.

Further objects and advantages of the invention will be described from the following description and the appended claims.

SUMMARY OF THE INVENTION

The present invention resides in a connector and deals more particularly in an improvement in such a connector wherein the contact spring is made radially deflectable and is coaxially disposed relative to the axial extent of the connecting body thereby reducing the length and width dimensions of the connector.

The connector more specifically comprises an elongated housing extending along a central axis, the housing has a generally cylindrical opening extending coaxially with the central axis. The opening in the housing is defined by first and second cylindrical surfaces each defined by a first diameter. An annular radially directed gap is disposed within the opening and is disposed axially between the first and second cylindrical surfaces, with the annular gap extending radially outwardly from the axis and beyond each of the first and second cylindrical surfaces. The gap has a given width as measured along the axis extending in the direction parallel thereto. A contact spring is provided and has a generally closed shape and is of a width sufficient to be received within the gap and has portions thereof extending inwardly toward the axis and into the opening.

Preferably, the annular gap in the housing is defined by an annular shoulder formed in the inner surface of the housing, the shoulder defines one of the first and second surfaces of the first diameter and defining a stepped annular surface of a second diameter wider than the opening and a collar member received within the second diameter in abutment against the spring.

Ideally, the spring is a metallic member having a general square shape as defined by four opposed sides each connected by a corner portion interposed therebetween and facing the central axis, and the spring on each side thereof having deformed portions which extend inwardly beyond the respective side face thereof and toward the central axis.

In one mode of the invention, the deformed portions are dome-like in shape and the spring has first and second end portions each defining a slight spacing therebetween. The spring is a generally closed shaped member defined by a small gap between first and second juxtaposed end portions of the spring. Preferably, the first and second end portions of the spring are disposed relative to one another at one corner of the square shape.

The four corners of the spring each are contained within the annular extending gap in the housing and a collar member is press fit into one end of a stepped bore forming in part the opening in the elongate housing and being axially spaced from the shoulder to form the gap. Preferably, the through opening in the connector is sized to receive a pace maker lead.

BRIEF DESCRIPTION OF THE DRAWINGS

FIG. 3 is an exploded view of the connector shown in FIG. 1.

FIG. 4 is a front elevation view of the connector housing as viewed along line 4—4 in FIG. 3.

DETAILED DESCRIPTION OF THE PREFERRED EMBODIMENTS

Figure 1:
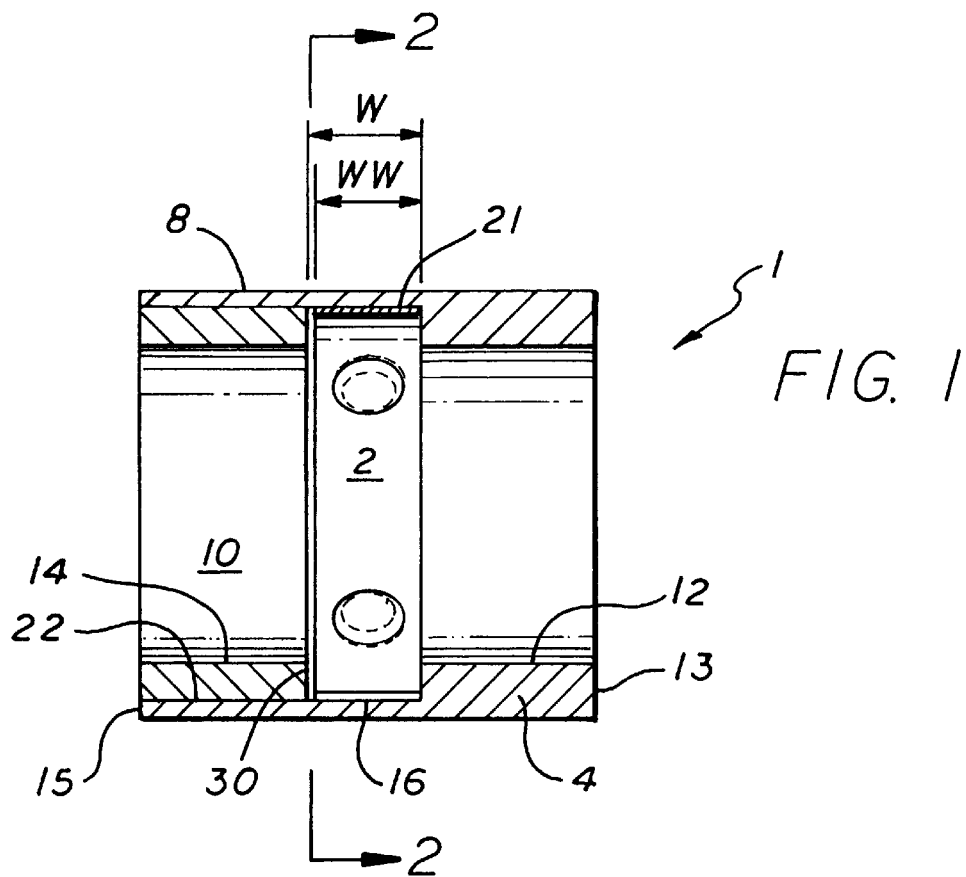
FIG. 1 is vertical section through the connector taken along line 1—1 in FIG. 2.

Referring now to FIG. 1, a connector referenced generally as element 1 is shown in the illustrative drawing. The connector 1 is comprised of an elongated housing 4 extending along a central axis CA. The housing 4 has a generally cylindrical opening 10 extending coaxially therethrough concentrically about the central axis CA and in which opening is located a contact spring 2 for engaging with the outer surface of a cylindrical lead (not shown) adapted to be slidingly received within the opening 10. The connector housing is formed from a conductive material, namely, rolled stainless steel, and is electrically connected to the electrical components of the pulse generator by a conductor ribbon, the free end of which being welded to the outer surface 8 of the housing 4.

The opening 10 in the housing 4 has an interrupted inner surface as defined by concentric first and second axially spaced cylindrical inner surfaces 12 and 14, respectively, together defining an annular radially directed gap 16 therebetween. As will be discussed in greater detail later, the contact spring 2 is located within the gap 16 to provide fail safe contact between the inserted lead and the housing 4. Also, for purposes of this discussion, the first cylindrical surface 12 will be referenced with respect to an associated one end 13 of the opening 10 while the second cylindrical surface 14 will be referenced with respect to the opposite other end 15 of the opening 10.

In the embodiment of FIG. 1, the opening 10 in the connector housing 4 is defined in part by a stepped bore 6 extending coaxially with the central axis CA. The stepped bore 6 (see FIG. 3) is defined by the first cylindrical surface 12 and a communicating larger diameter cylindrical surface 22. The first cylindrical surface 12 has a diameter D1 which is correspondingly sized and shaped to receive the outer surface of a lead therein and is separated from the concentrically disposed diamentrically larger cylindrical inner surface 22 of the stepped bore 6 by an orthogonally oriented annular shoulder 18 which provides an abutment face against which the contact spring 2 is maintained with respect to one possible direction of movement.

The larger diameter inner cylindrical surface 22 of the stepped bore 6 has an inner diameter D2 which is adapted to receive an annular locking collar 24 therewithin. The locking collar 24 has an inner cylindrical surface S which when the collar is fitted into the housing 4, defines the second cylindrical inner surface 14 of the connector.

The locking collar 24 further has an outer cylindrical surface 28 of an outer diameter D3 which is sized so that the collar 24 can be press fit within the larger cylindrical inner surface 22 of the stepped bore 6 to effect an interference fit therebetween. In so doing, the leading end 30 of the locking collar 24 is pressed into open end 15 of the connector and along the cylindrical surface 22 of the stepped bore 6 a distance sufficient to leave the gap 16 of a width W between the collar end 30 and the annular shoulder 18 of the bore extending in a direction parallel to the axis CA. As mentioned, the inner surface S of the collar 24 is defined by the second cylindrical surface 14 and has the same diameter D1 as the first cylindrical surface 12.

The contact spring 2 is maintained in axial abutment between the shoulder 18 of the bore 6 and the leading end 30 of the collar 24. The annular gap 16 extends radially outwardly beyond the axially spaced first and second cylindrical surfaces 12 and 14 of the central opening 10 and stops at an end wall 21 defined by the larger diameter cylindrical surface 22 of the stepped bore 6.

Figure 2:
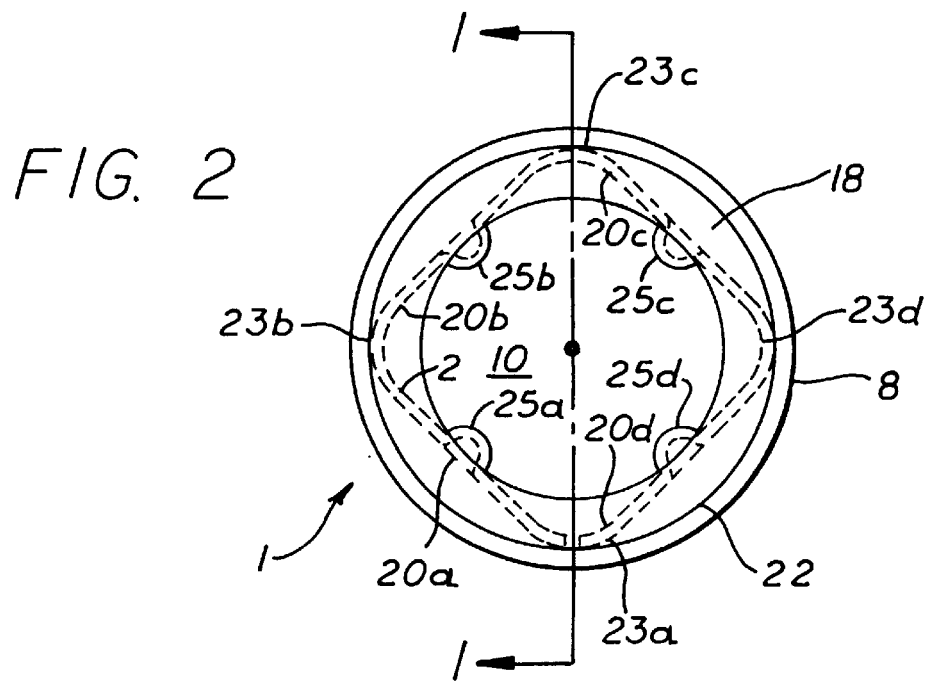
FIG. 2 is vertical section through the connector taken along line 2—2 in FIG. 1.

Referring now to FIGS. 2 and 4, and in particular to the contact spring 2, it should be seen that the contact spring 2 is a substantially square-like member having four sides respectively labeled 20a–20d each redirected ninety degrees at connected corners 23a–23d, respectively. The spring 2 has a generally closed shape and is of a width WW sufficient to be received widthwise within the gap 16 in the housing 4.

Located approximately mid-length of the sides 20a–20d is a raised partially spherically shaped projection 25a–25d which has a generally circular base formed by a deformed localized region of sheet metal also directed radially spherically inwardly toward the central axis CA. Each projection 25a–25d has a radius defining its circular base extending in a first plane parallel to the central axis CA equal to approximately 0.02 inch and has a radius extending in a second plane orthogonally disposed to the first plane and defining the partially spherical shape of the projection of about 0.01 inches.

Figure 5:
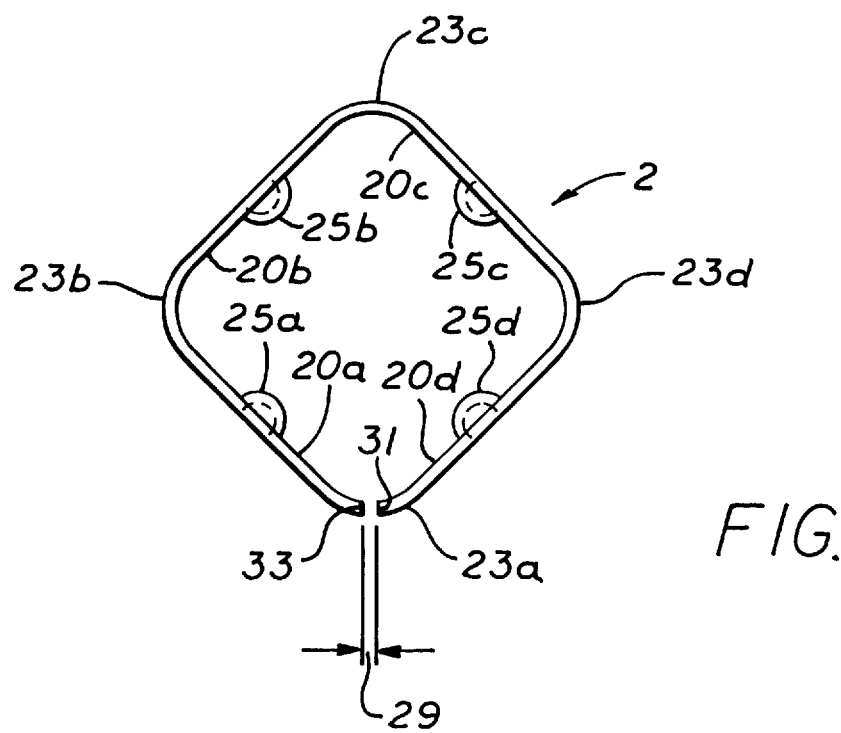
FIG. 5 is a plan view of the contact spring element shown apart from the connector assembly.

The contact spring 2 is formed from a stamped, formed sheet metal strip having a width WW of approximately 0.04 inches and is bent in the illustrated square shaped configuration. The sheet metal forming this spring 2 has a thickness of about 0.003 inches and is a generally closed shape member defined by opposed free ends 31 and 33, which in the relaxed condition, define a gap referenced in FIG. 5 as 29. In the assembled condition of the connector and before the lead is introduced into the opening 10, the free ends of the spring maintain a spacing of approximately 0.005 inch.

Figure 6:
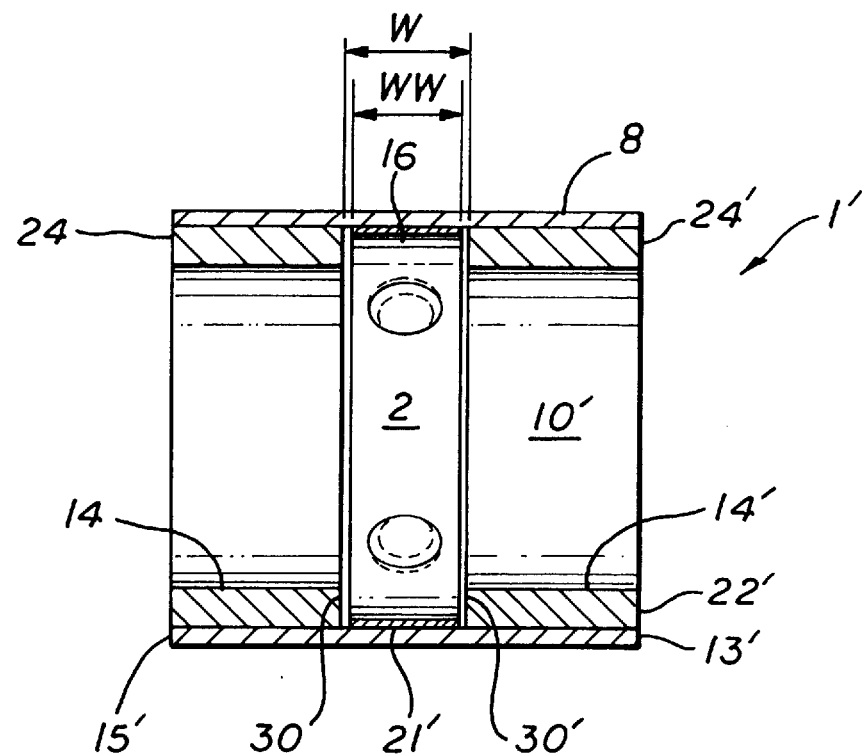
FIG. 6 is vertical section through an alternative embodiment of the connector assembly.

In the assembled condition, the contact spring 2 is axially locked within the connector housing 4 as illustrated in FIGS. 1 and 6, and further is located coaxially with the central axis CA such that the projections 25a–25d extend inwardly beyond the inner diameter D1 of the first and second inner cylindrical surfaces 12 and 14. In this way, the projections 25a–25d radially yieldably interfere with the path followed by a lead when it is inserted into the opening 10. Conversely, the axially locked condition of the contact spring 2 is an important feature of the invention because it prevents possible pullout of the spring with the extraction of the lead.

As illustrated in FIG. 3, the collar member is a generally hollow cylindrical member which is a force fit inwardly into the one end 15 of the opening 10 to maintain the contact spring within the gap 16 of the connector. This is done, as best illustrated in FIG. 2, by orienting the square shape of the spring so that the corners thereof are each located within the annular gap 16 to maintain the spring therewithin so that the spring is maintained between the opposed annular end face of the collar member 16 and the stepped surface 18 of the inner bore 6.

Referring now to the illustrated embodiment shown in FIG. 6, it should be seen that the connector housing 4' in this embodiment is comprised of an opening 10' defined by two collar members fitted within a uniform diameter bore extending throughout the length of the connector. That is, the gap 16 in FIG. 6 is formed by providing two locking collars 24, 24' each press fit into the opening 22' in the housing through respective opposite ends 13' and 15' in the housing 4' so as to be spaced apart from one another to form the gap 16 for the contact spring 2.

Accordingly, the invention has been described by way of illustration rather than limitation.

What is claimed is:

1. A connector comprising:

an elongated housing extending along a central axis;

said housing having a generally cylindrical opening extending coaxially with said central axis;

said opening in said housing being defined by first and second cylindrical surfaces each defined by a first diameter, an annular radially directed gap disposed within said opening and extending axially between said first and second cylindrical surfaces, said annular gap extending radially outwardly from said central axis and outwardly beyond each of said first and second cylindrical surfaces, said gap having a given width as measured along said axis extending in a direction parallel thereto;

a spring having a width sufficient to be received within said gap and having at least one portion extending perpendicularly to said central axis and into said opening;

wherein said spring being a stamped formed metallic spring having a generally closed shape as defined by four opposed sides each connected by a corner portion interposed therebetween and facing said central axis; and said spring on each side thereof carrying said at least one portion which is a deformed portion of an associated one of said sides extending inwardly beyond the respective side thereof and toward said central axis.

2. A connector, as defined in claim 1, further characterized in that said annular gap in said housing is defined by an annular shoulder formed in the inner surface of said housing, said shoulder defining one of said first and second surfaces of said first diameter and defining a stepped annular surface of a second diameter wider than said opening and a collar member received within said stepped annular surface of said second diameter in abutment against said spring.

3. A connector, as defined in claim 1, further characterized in that said deformed portions are dome-like in shape and said spring has first and second end portions each defining a slight spacing therebetween.

4. A connector, as defined in claim 3, further characterized in that said first and second end portions of said spring being disposed to one another at one corner of said square shape.

5. A connector, as defined in claim 4, further characterized by said four corners of said spring each being contained within said annular extending gap in said housing.

6. A connector, as defined in claim 5, further characterized in that said opening is a bore with a uniform diameter and two collar members are press fit into said opening at opposite ends at a spaced distance thereof to effect said gap.

7. A connector, as defined in claim 5, further characterized by said housing further including said opening being defined by a stepped bore.

8. A connector, as defined in claim 7, further characterized in that said cylindrical opening in said connector being sized to receive a pace maker lead.

9. A connector comprising:

an elongated generally cylindrical housing extending along a central axis; said housing having a generally cylindrical opening extending coaxially with said central axis; said opening in said housing being defined by first and second cylindrical surfaces each defined by a first diameter, the first cylindrical surface being defined by one surface of a stepped bore formed in said housing and said second cylindrical surface being defined by an inner surface of an annular collar received within another wider surface of said stepped bore; an annular radially directed gap disposed within said opening and extending axially between said first and second cylindrical surfaces, said annular gap extending radially outwardly from said central axis and beyond each of said first and second cylindrical surfaces, said gap having a given width as measured along said central axis extending in a direction parallel thereto;

a spring having means extending perpendicularly to said central axis for engaging a lead inserted into said opening in said housing;

wherein said spring being a stamped formed metallic spring having a general closed shape as defined by four opposed sides each connected by a corner portion interposed therebetween and facing said central axis; and said spring on each side thereof carrying said lead engaging means which are deformed portions of said sides extending inwardly beyond the respective side thereof and toward said central axis.

10. A connector, as defined in claim 9, further characterized in that said deformed portions are dome-like in shape and said spring has first and second end portions each defining a slight spacing therebetween.

11. A connector, as defined in claim 10, further characterized in that said first and second end portions of said spring being disposed to one another at one corner of said square shape.

12. A connector, as defined in claim 11, further characterized by said four corners of said spring each being contained within said annular extending gap in said housing.

* * * * *